(12) United States Patent
Kimchy et al.

(10) Patent No.: US 9,844,354 B2
(45) Date of Patent: Dec. 19, 2017

(54) INTRA-LUMEN POLYP DETECTION

(75) Inventors: Yoav Kimchy, Haifa (IL); Yitzak Klein, Kiryat Yam (IL); Gideon Baum, Haifa (IL); Rafi Sommer, Nesher (IL)

(73) Assignee: CHECK-CAP LTD., Isfyia (IL)

( * ) Notice: Subject to any disclaimer, the term of this patent is extended or adjusted under 35 U.S.C. 154(b) by 788 days.

(21) Appl. No.: 12/525,672

(22) PCT Filed: Feb. 6, 2008

(86) PCT No.: PCT/IL2008/000163
§ 371 (c)(1),
(2), (4) Date: Nov. 17, 2009

(87) PCT Pub. No.: WO2008/096358
PCT Pub. Date: Aug. 14, 2008

(65) Prior Publication Data
US 2010/0174184 A1 Jul. 8, 2010

Related U.S. Application Data

(60) Provisional application No. 60/899,640, filed on Feb. 6, 2007.

(51) Int. Cl.
*A61B 6/00* (2006.01)

(52) U.S. Cl.
CPC ............ *A61B 6/4057* (2013.01); *A61B 6/425* (2013.01); *A61B 6/4258* (2013.01); *A61B 6/485* (2013.01)

(58) Field of Classification Search
CPC .. G01T 1/161; A61B 6/4258; A61B 2019/542
(Continued)

(56) References Cited

U.S. PATENT DOCUMENTS 3,967,122 A * 6/1976 Ashe .................... G01N 23/223
250/367
4,217,045 A 8/1980 Ziskind
(Continued)

FOREIGN PATENT DOCUMENTS

EP 0390478 A1 10/1990
WO 00/49958 8/2000
(Continued)

OTHER PUBLICATIONS

Brochard et al., "Estimation of movement parameters of 3D textured surfaces using the autocorrelation function", Pattern Recognition Letters, 24:2031-2045 (2003).
(Continued)

*Primary Examiner* — Hien Nguyen
(74) *Attorney, Agent, or Firm* — Soroker Agmon Nordman

(57) ABSTRACT

An apparatus and a method for detecting clinically-relevant features of the gastrointestinal (GI) tract of a subject are disclosed. The apparatus includes a capsule to be swallowed by a subject and passing through the GI tract of the subject, a capsule housing, a radiation source emitting radiation, a rotatable collimator configured to rotate with respect to the housing and to collimate the radiation emitted by the radiation source, and a radiation detector configured to detect particles, such as photons, gamma radiation, beta radiation and electrons photons generated responsive to the emitted radiation. The apparatus also includes a control unit configured to analyze data regarding the photons. Movement of the capsule in the GI tract can be detected from a comparison between at least two images acquired with the apparatus. The radiation source, radiation detector and control unit may advantageously be integrated inside a single housing.

20 Claims, 3 Drawing Sheets

(58) Field of Classification Search
USPC .......................................................... 600/436
See application file for complete search history.

(56) References Cited

U.S. PATENT DOCUMENTS

| | | | |
|---|---|---|---|
| 4,503,328 A * | 3/1985 | Neufeld | 250/262 |
| 4,689,621 A | 8/1987 | Kleinberg | |
| 4,726,381 A | 2/1988 | Jones | |
| 4,763,658 A | 8/1988 | Jones | |
| 4,765,339 A | 8/1988 | Jones | |
| 4,774,955 A | 10/1988 | Jones | |
| 4,803,992 A | 2/1989 | Lemelson | |
| 4,844,076 A | 7/1989 | Lesho et al. | |
| 4,883,063 A | 11/1989 | Bernard et al. | |
| 5,003,980 A | 4/1991 | Loo et al. | |
| 5,353,807 A | 10/1994 | DeMarco | |
| 5,372,133 A | 12/1994 | Hogen Esch | |
| 5,395,366 A | 3/1995 | D'Andrea et al. | |
| 5,415,181 A | 5/1995 | Hogrefe et al. | |
| 5,422,926 A | 6/1995 | Smith et al. | |
| 5,604,531 A | 2/1997 | Iddan et al. | |
| 5,721,462 A | 2/1998 | Shanks | |
| 5,778,882 A | 7/1998 | Raymond et al. | |
| 5,792,053 A | 8/1998 | Skladnev et al. | |
| 5,800,350 A | 9/1998 | Coppleson et al. | |
| 5,829,437 A | 11/1998 | Bridges | |
| 5,833,603 A | 11/1998 | Kovacs et al. | |
| 5,842,977 A | 12/1998 | Lesho et al. | |
| 5,853,005 A | 12/1998 | Scanlon | |
| 5,993,378 A | 11/1999 | Lemelson | |
| 6,134,300 A | 10/2000 | Trebes et al. | |
| 6,169,914 B1 | 1/2001 | Hovland et al. | |
| 6,173,201 B1 | 1/2001 | Front | |
| 6,240,312 B1 | 5/2001 | Alfano et al. | |
| 6,254,548 B1 | 7/2001 | Ishikawa et al. | |
| 6,317,927 B1 | 11/2001 | Lai et al. | |
| 6,324,418 B1 | 11/2001 | Crowley et al. | |
| 6,343,227 B1 | 1/2002 | Crowley | |
| 6,353,658 B1 | 3/2002 | Trebes et al. | |
| 6,368,275 B1 | 4/2002 | Sliwa et al. | |
| 6,368,331 B1 | 4/2002 | Front et al. | |
| 6,400,974 B1 | 6/2002 | Lesho | |
| 6,423,056 B1 | 7/2002 | Ishikawa et al. | |
| 6,428,469 B1 | 8/2002 | Iddan et al. | |
| 6,428,531 B1 | 8/2002 | Visuri et al. | |
| 6,428,569 B1 | 8/2002 | Brown | |
| 6,440,069 B1 | 8/2002 | Raymond et al. | |
| 6,453,199 B1 | 9/2002 | Kobozev | |
| 6,567,687 B2 | 5/2003 | Front et al. | |
| 6,582,365 B1 | 6/2003 | Hines et al. | |
| 6,584,348 B2 | 6/2003 | Glukhovsky | |
| 6,607,301 B1 | 8/2003 | Glukhovsky et al. | |
| 6,629,776 B2 | 10/2003 | Bell et al. | |
| 6,632,175 B1 | 10/2003 | Marshall | |
| 6,709,387 B1 | 3/2004 | Glukhovsky et al. | |
| 6,719,684 B2 | 4/2004 | Kim et al. | |
| 6,764,440 B2 | 7/2004 | Iddan et al. | |
| 6,776,165 B2 | 8/2004 | Jin | |
| 7,824,559 B2 * | 11/2010 | Dorian et al. | 210/782 |
| 8,636,648 B2 * | 1/2014 | Gazdzinski | 600/109 |
| 2001/0038831 A1 | 11/2001 | Park et al. | |
| 2001/0041835 A1 | 11/2001 | Front et al. | |
| 2001/0051766 A1 * | 12/2001 | Gazdzinski | 600/309 |
| 2002/0026108 A1 | 2/2002 | Colvin, Jr. | |
| 2002/0099310 A1 | 7/2002 | Kimchy et al. | |
| 2003/0139661 A1 * | 7/2003 | Kimchy et al. | 600/407 |
| 2004/0015075 A1 | 1/2004 | Kimchy et al. | |
| 2004/0054248 A1 | 3/2004 | Kimchy et al. | |
| 2004/0054278 A1 | 3/2004 | Limchy et al. | |
| 2004/0120557 A1 * | 6/2004 | Sabol et al. | 382/128 |
| 2004/0204646 A1 | 10/2004 | Negler et al. | |
| 2004/0250124 A1 | 12/2004 | Chesla et al. | |
| 2005/0055174 A1 | 3/2005 | David et al. | |
| 2005/0205792 A1 | 9/2005 | Rousso et al. | |
| 2005/0266074 A1 | 12/2005 | Zilberstein et al. | |
| 2006/0033029 A1 | 2/2006 | Popper | |
| 2006/0065836 A1 * | 3/2006 | Tsuchiya et al. | 250/363.1 |
| 2006/0109953 A1 * | 5/2006 | Walter et al. | 378/5 |
| 2006/0217593 A1 | 9/2006 | Gilad et al. | |
| 2006/0237652 A1 | 10/2006 | Kimchy et al. | |
| 2007/0156047 A1 | 7/2007 | Nagler et al. | |

FOREIGN PATENT DOCUMENTS

| | | | |
|---|---|---|---|
| WO | 01/62134 | A2 | 8/2001 |
| WO | 02/16965 | A2 | 2/2002 |
| WO | 02/058531 | A2 | 8/2002 |
| WO | 2004/042546 | A1 | 5/2004 |
| WO | 2005/058129 | A2 | 6/2005 |
| WO | 2005/067383 | A2 | 7/2005 |
| WO | 2005/104939 | A2 | 11/2005 |
| WO | 2005/112895 | A2 | 12/2005 |

OTHER PUBLICATIONS

Camilleri et al., "Human gastric emptying and colonic filling of solids characterized by a new method", Am. J. Physiol., 257:G284-G290 (1989).

Compton, Arthur H., "A Quantum Theory of the Scattering of X-Rays by Light Elements", Physical Review, 21(5):483-502 (1923).

Compton, Arthur H., "The Spectrum of Scattered X-Rays", Physical Review, 22(5):409-413 (1923).

Haga et al., "A Miniature X-Ray Tube", Applied Physics Letters, 84(12):2208-2210 (2004).

Madsen et al., "Gastrointestinal Transit of Technetium-99m-Labeled Cellulose Fiber and Indium-111-Labeled Plastic Particles", Journal of Nuclear Medicine, 30:402-406 (1989).

Proano et al., "Transit of Solids through the Human Colon: Regional Quantification in the Unprepared Bowel", Am. J. Physiol., 258:G856-G862 (1990).

Tartari et al., "Compton Scattering Elemental Imaging of a Deep Layer Performed with the Principal Component Analysis", Proc. of the 15th World Conference on Non-Destructive Testing, Conservation and Restoration in Art and Architecture, Rome, Oct. 15-21, 2000, 7 pages.

"X-Ray Contrast Medium", Encyclopaedia of Medical Imaging, vol. 1, www.medcyclopaedia.com., 5 pages.

Caner B.E. et al., "Functional assessment of human gastrointestinal tract using 99Tcm-latex particles", Abstract only, Nucl. Med. Commun., 12(6):539-544 (1991).

Gutman G. et al., "A novel needle-based miniature x-ray generating system". Abstract only, Phys. Med. Biol., 49(20):4677-4688 (2004).

\* cited by examiner

INTRA-LUMEN POLYP DETECTION

CROSS-REFERENCES TO RELATED APPLICATIONS

The present patent application is a national stage application under 35 U.S.C. 371 of PCT International Application No. PCT/IL2008/000163, filed Feb. 6 2008, which designated the United States and has been published as International Publication No. WO 2008/096358, and on which priority is claimed under 35 U.S.C. §120, and which claims the benefit of U.S. Provisional Patent Application No. 60/899,640 to Kimchy et al., filed on Feb. 6, 2007, the contents of which are incorporated herein by reference in their entirety as if fully set forth herein.

FIELD OF THE INVENTION

The present invention relates generally to the field of detection of conditions of a body lumen, and specifically to a swallowable device that travels in the colon and detects anatomical anomalies.

BACKGROUND OF THE INVENTION

Colorectal cancer is one of the leading causes of death in the Western world. Clinical evidence suggests that early detection of primary colorectal cancer leads to a 90% or better 5-year survival rate, while detection of the disease when it has already metastasized leads to a poorer prognosis, with a 50% or less 5-year survival rate and a 30% recurrence rate. Colorectal cancer screening and early detection have a substantial positive impact on the prognosis of this malignancy.

PCT Publication WO 05/058129 to Kimchy ("the '129 Publication"), which is incorporated herein by reference, describes a capsule, adapted to be swallowed by a subject, the capsule including (a) at least one radiation source, adapted to emit radiation having an energy of at least 10 keV, and (b) at least one photon detector, adapted to detect photons generated responsively to the emitted radiation, the photons having an energy of at least 10 keV. The apparatus additionally includes a control unit, adapted to analyze data regarding the photons in order to generate information useful for identifying a clinically-relevant feature of a gastrointestinal (GI) tract of the subject.

The following references, all of which are incorporated herein by reference, may be of interest:

U.S. Pat. No. 6,240,312 to Alfano et al.
U.S. Pat. No. 5,422,926 to Smith et al.
U.S. Pat. No. 5,003,980 to Loo et al.
U.S. Pat. No. 4,217,045 to Ziskind
U.S. Pat. No. 6,567,687 to Front et al.
U.S. Pat. No. 6,173,201 to Front
U.S. Pat. Nos. 6,134,300 and 6,353,658 to Trebes et al.
U.S. Pat. No. 5,721,462 to Shanks
US Patent Application Publication 2002/0099310 to Kimchy et al.
US Patent Application Publication 2007/0156047 to Nagler et al.
US Patent Application Publication 2006/0237652 to Kimchy et al.
US Patent Application Publication 2005/0266074 to Zilberstein et al.
US Patent Application Publication 2005/0205792 to Rousso et al.
US Patent Application Publication 2004/0054278 to Kimchy et al.
US Patent Application Publication 2004/0054248 to Kimchy et al.
US Patent Application Publication 2004/0015075 to Kimchy et al.
US Patent Application Publication 2003/0139661 to Kimchy et al.
US Patent Application Publication 2001/0041835 to Front et al.
U.S. Pat. No. 6,368,331 to Front et al.
US Patent Application Publication 2006/0033029 to Popper
US Patent Application Publication 2005/0055174 to David et al.
US Patent Application Publication 2004/0204646 to Nagler et al.
PCT Publication WO 05/112895 to Zilberstein et al.
PCT Publication WO 05/104939 to Nagler et al.
PCT Publication WO 05/067383 to Rousso et al.
PCT Publication WO 04/042546 to Kimchy et al.
PCT Publication WO 02/16965 to Kimchy et al.
PCT Publication WO 01/62134 to Front et al.
PCT Publication WO 00/49958 to Front et al. PCT Publication WO05058129A2 to Kimchy.
PCT Publication WO 02/058531 to Kimchy, et al.
Brochard J et al., "Estimation of movement parameters of 3D textured surfaces using the autocorrelation function," Pattern Recognition Letters 24(12):2031-2045 (2003)
Camilleri M et al., "Human gastric emptying and colonic filling of solids characterized by a new method," Am J Physiol 257(2 Pt 1):G284-G290 (1989)
Caner BE et al., "Functional assessment of human gastrointestinal tract using 99Tcm-latex particles," Nucl Med Commun 12(6):539-544 (1991)
Compton, Arthur H., Phys. Rev. 21,483; 22,409 (1923)
Gutman G et al., "A novel needle-based miniature x-ray generating system," Phys Med Biol 49:4677-4688 (2004)
Haga A et al., "A miniature x-ray tube," Applied Physics Letters 84(12):2208-2210 (2004)
Madsen JL et al., "Gastrointestinal transit of technetium-99m-labeled cellulose fiber and indium-111-labeled plastic particles," J Nucl Med 30(3):402-406 (1989)
Pais, Abraham, 'Subtle is the Lord . . . ': The Science and the Life of Albert Einstein, Oxford (1982)
Proano M et al., "Transit of solids through the human colon: regional quantification in the unprepared bowel," Am J Physiol 258(6 Pt 1):-G862 (1990)
Tartan A et al., "Compton scattering elemental imaging of a deep layer performed with the principal component analysis," Proceedings of the 15th World Conference on Non-Destructive Testing, Conservation and Restoration in Art and Architecture, Rome (Oct. 15-21, 2000)
"X-ray contrast medium," Medcyclopaedia™ (www.medcyclopaedia.com), from The Encyclopaedia of Medical Imaging Volume I The following US patents, all of which are incorporated herein by reference, may be of interest:

U.S. Pat. Nos. 4,689,621, 4,726,381, 4,763,658, 4,765, 339, 4,774,955, 4,803,992, 4,844,076, 4,883,063, 5,353,807, 5,372,133, 5,395,366, 5,415,181, 5,604,531, 5,778,882, 5,792,053, 5,800,350, 5,829,437, 5,833,603, 5,842,977, 5,853,005, 5,993,378, 6,169,914, 6,240,312, 6,254,548, 6,317,927, 6,324,418, 6,343,227, 6,368,275, 6,400,974, 6,423,056, 6,428,469, 6,428,531, 6,440,069, 6,453,199, 6,582,365, 6,584,348, 6,607,301, 6,629,776, 6,632,175, 6,709,387, 6,719,684, 6,764,440, 6,776,165

SUMMARY OF THE INVENTION

Embodiments of the present invention are directed at the detection of polyps and other clinically relevant features that may harbor the potential for cancer of the gastrointestinal (GI) tract, particularly colorectal cancer.

In some embodiments, a subject undergoes a colorectal cancer screening procedure. Typically, the subject swallows a radiopaque contrast agent (such as barium sulphate or an iodine-based contrast agent). Subsequently, and typically after a waiting period, the subject swallows a capsule comprising a gamma, x-ray or beta radiation source and radiation detectors. As the capsule travels through the GI tract, the radiation source "illuminates" the vicinity of the capsule. The GI contents (including the contrast agent), GI wall, and tissue outside of the GI tract act as a scattering medium for the emitted radiation, typically primarily through the process of Compton scattering. The scattered photons then travel back through the GI contents, which include the radiopaque contrast agent. In some embodiments, radiation detectors on the capsule also detect x-ray fluorescence (XRF) photons emitted from the radiopaque contrast agent, back-scattered beta electrons and/or electrons that are generated as a result of the emitted radiation. Count rate information regarding Compton backscattered photons, XRF photons, and/or electrons is typically transmitted to an external recording unit worn by the subject.

The count rates collected by each detector per unit time interval are analyzed. These data are presented to a physician in a manner (such as a constructed image) that enables him to assess the likelihood that there is a polyp or some other anatomical deformation in the GI tract. In some embodiments, the data are also analyzed to indicate a general area of the colon where such a deformation may exist. These polyps or anatomical anomalies may be the result of a tumor beginning to grow within the GI tract. In some embodiments, the apparatus enables a physician to distinguish between a) tubular and villous polyps, and b) neoplastic polyps, and/or between polyps which have stalks and polyps which do not have stalks. If based on the presented data the physician suspects the presence of a polyp or some other anatomical anomaly that may be cancerous or pre-cancerous, the subject is typically referred for further diagnostic testing, such as colonoscopic examination.

There is therefore provided in accordance with an embodiment of the present invention, apparatus, including:
a capsule, configured to be swallowed by a subject and to pass through a GI tract of the subject, and including:
    a capsule housing;
    at least one radiation source, configured to emit radiation;
    a rotatable collimator configured to rotate with respect to the housing and to collimate the radiation emitted by the radiation source; and
    at least one photon detector, configured to detect photons generated responsively to the emitted radiation,
the apparatus including a control unit configured to analyze data regarding the photons in order to generate information useful for identifying a clinically-relevant feature of the GI tract of the subject.

In an embodiment, the control unit is configured to detect that the capsule has reached an area of clinical interest within the GI tract, and to initiate rotation of the collimator in response to detecting that the capsule has reached the area of clinical interest.

In an embodiment, the collimator is rotatable with respect to the housing through at least 270 degrees.

In an embodiment, the collimator includes two or more rotatable collimators, each of which collimators is rotatable with respect to the housing through less than 360 degrees.

In an embodiment, the photon detector is configured to rotate with respect to the housing and to detect photons generated responsively to the emitted radiation.

In an embodiment, the detector is rotatable through at least 270 degrees.

In an embodiment, the detector includes two or more rotatable detectors, each of which detectors is rotatable with respect to the housing through less than 360 degrees.

There is additionally provided in accordance with an embodiment of the present invention, apparatus, including:
a capsule configured to be swallowed by a subject and configured to emit radiation, and to detect in response thereto a first and a second signal inside a GI tract of the subject,
the apparatus including a control unit configured to:
    process the first signal to generate a first image of the GI tract in a region in which the first signal was detected;
    process the second signal to generate a second image of the GI tract in a region in which the second signal was detected; and
    detect movement of the capsule by comparing the first and second images.

There is further provided in accordance with an embodiment of the present invention, apparatus including:
a capsule, configured to be swallowed by a subject, and including:
    at least one beta radiation source; and
    at least one photon detector, configured to detect photons generated responsively to radiation emitted from the beta radiation source,
the apparatus including a control unit configured to derive an indication of tissue density in a vicinity of the capsule by analyzing data regarding the detected photons.

In an embodiment, the control unit is configured to distinguish between a) tubular and villous polyps, and b) neoplastic polyps, in response to the indication of tissue density.

In an embodiment, the apparatus further includes at least one electron detector, configured to detect electrons generated responsively to radiation emitted from the beta radiation source, and the control unit is configured to derive an indication of tissue density in a vicinity of the capsule by analyzing data regarding the detected photons and the detected electrons.

There is additionally provided in accordance with an embodiment of the present invention, apparatus, including:
a capsule, configured to be swallowed by a subject, and including:
    at least one beta radiation source; and
    at least one electron detector, configured to detect electrons generated responsively to radiation emitted from the beta radiation source,
the apparatus including a control unit configured to derive an indication of tissue density in a vicinity of the capsule by analyzing data regarding the detected electrons.

In an embodiment, the control unit is configured to distinguish between a) tubular and villous polyps, and b) neoplastic polyps, in response to the indication of tissue density.

There is further provided in accordance with an embodiment of the present invention, apparatus, including:
a capsule, configured to be swallowed by a subject, and including:
at least one radiation source configured to emit radiation; and
at least one photon detector configured to detect Compton backscattered photons generated responsively to the radiation emitted by the radiation source,
the apparatus including a control unit configured to distinguish between a) tubular and villous polyps, and b) neoplastic polyps, by deriving an indication of tissue density in a vicinity of the capsule by analyzing data regarding the detected Compton backscattered photons.

In an embodiment, the radiation source is configured to emit one or more radioactive particles selected from the group consisting of: x-ray photons, gamma photons, and beta electrons.

There is further provided in accordance with an embodiment of the present invention, apparatus, including:
a capsule, configured to be swallowed by a subject, and including:
at least one radiation source configured to emit radiation; and
at least one photon detector configured to detect Compton backscattered photons and XRF photons generated responsively to the radiation emitted by the radiation source,
the apparatus including a control unit configured to distinguish between a) tubular and villous polyps, and b) neoplastic polyps, by deriving an indication of tissue density in a vicinity of the capsule by analyzing data regarding the detected Compton backscattered photons and XRF photons.

In an embodiment, the radiation source is configured to emit one or more radioactive particles selected from the group consisting of: x-ray photons, gamma photons, and beta electrons.

There is additionally provided in accordance with an embodiment of the present invention, apparatus, including:
a capsule, configured to be swallowed by a subject, and including:
at least one radiation source configured to emit radiation; and
at least one detector configured to detect electrons generated responsively to the radiation emitted by the radiation source,
the apparatus including a control unit configured to distinguish between a) tubular and villous polyps, and b) neoplastic polyps, by deriving an indication of tissue density in a vicinity of the capsule by analyzing data regarding the detected beta radiation.

In an embodiment, the radiation source is configured to emit one or more radioactive particles selected from the group consisting of: x-ray photons, gamma photons, and beta electrons.

There is further provided in accordance with an embodiment of the present invention, apparatus, including:
a capsule, configured to be swallowed by a subject, and including:
at least one radiation source configured to emit radiation; and
at least one detector configured to detect electrons and photons generated responsively to the radiation emitted by the radiation source,
the apparatus including a control unit configured to distinguish between a) tubular and villous polyps, and b) neoplastic polyps, by deriving an indication of tissue density in a vicinity of the capsule by analyzing data regarding the detected beta radiation.

There is additionally provided in accordance with an embodiment of the present invention, apparatus, including:
a capsule, configured to be swallowed by a subject, and including:
a radiation source; and
a rotatable shield configured to cover the radiation source when the shield is not rotating and configured to uncover the radiation source when the shield is rotating at a rotation rate that exceeds a threshold,
the apparatus including a control unit configured to rotate the shield at a rotation rate that exceeds the threshold.

In an embodiment, the rotatable shield is configured to uncover the radiation source due to centrifugal force induced by the rotation of the shield.

There is further provided in accordance with an embodiment of the present invention, apparatus, including:
a capsule, configured to be swallowed by a subject and to advance through a GI tract of the subject, and including:
a first antenna configured to emit at first and second times, respective first and second RF pulses, while the capsule is inside the GI tract; and
a second antenna configured to detect the respective RF pulses,
the apparatus including a control unit configured to identify movement of the capsule through the GI tract in response to a change in the detected first and second RF pulses.

There is additionally provided, in accordance with an embodiment of the present invention, apparatus, including:
a capsule, configured to be swallowed by a subject and to advance through a GI tract of the subject, and including two electrodes configured to create a voltage drop therebetween at first and second times, while the capsule is inside the GI tract,
the apparatus including a control unit configured to identify movement of the capsule through the GI tract in response to a change in current flowing between the electrodes at the first and second times.

There is further provided in accordance with an embodiment of the present invention, apparatus, including:
a capsule, configured to be swallowed by a subject and to advance through a GI tract of the subject, and including a sensor configured to detect a disposition of the capsule,
the apparatus including a control unit configured to determine that the capsule has been expelled from the subject's anus in response to the detected disposition.

In an embodiment, the capsule is configured to acquire data regarding the GI tract while the capsule advances through the GI tract, and the control unit is configured to download the detected data from the capsule in response to detecting that the capsule has been expelled from the subject's anus.

There is additionally provided in accordance with an embodiment of the present invention, apparatus, including:
a capsule, configured to be swallowed by a subject and to pass through a GI tract of the subject, and including:
at least one radiation source; and
at least one photon detector, configured to detect photons generated responsively to radiation emitted from the radiation source,
the apparatus including a control unit configured to distinguish between a polyp with a stalk and a polyp without a stalk, the polyps being within the subject's GI tract, by analyzing data regarding the detected photons.

In an embodiment, the radiation source includes a beta radiation source.

There is further provided in accordance with an embodiment of the present invention, apparatus, including:
a capsule, configured to be swallowed by a subject and to pass through a colon of the subject, and including:
at least one radiation source configured to emit radiation; and
at least one photon detector configured to detect Compton backscattered photons and XRF photons generated responsively to the radiation emitted by the radiation source,
the apparatus including a control unit configured to estimate a distance between the capsule and a wall of the colon by (a) analyzing Compton photon flux and XRF photon flux of the detected photons at multiple closely-spaced points along the colon, and (b) assuming a low level of change of concentration of contrast agent in the subject's colon at the closely-spaced points.

There is additionally provided, in accordance with an embodiment of the present invention, a method, including:
administering a contrast agent to a subject;
administering a capsule to the subject, the capsule being configured to be swallowed by the subject and to advance through a colon of the subject;
emitting radiation from the capsule, within the subject's colon, through the contrast agent;
detecting photon fluxes of Compton backscattered photons and XRF photons generated responsively to the emitted radiation at multiple closely-spaced points along the colon; and
determining a distance between the capsule and a wall of the colon by analyzing the detected Compton and XRF photon fluxes and assuming a low level of change of concentration of the contrast agent in the subject's colon at the closely-spaced points In an embodiment, determining the distance includes determining an average contrast agent concentration based on the fluxes detected at the closely-spaced points.

In an embodiment, detecting the photon fluxes includes detecting the photon fluxes when the capsule is at each of multiple closely-spaced points, the points being within a single haustrum of the colon.

In an embodiment, detecting the photon fluxes includes detecting the photon fluxes when the capsule is at each of multiple closely-spaced points, the points being within a length of 20 mm to 40 mm of the colon.

The present invention will be more fully understood from the following detailed description of embodiments thereof, taken together with the drawings, in which:

DETAILED DESCRIPTION OF EMBODIMENTS

Figure 1:
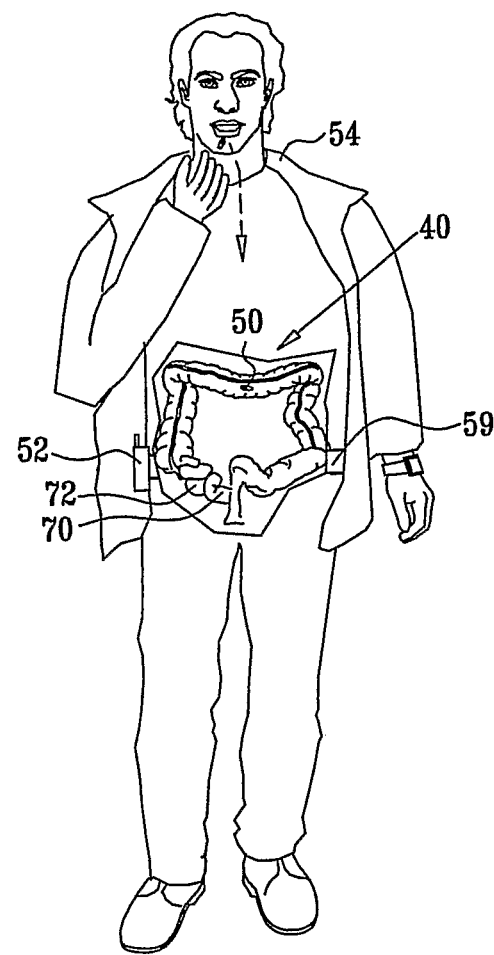
FIG. 1 is a schematic illustration of a screening system, in accordance with an embodiment of the present invention.

Reference is made to FIG. 1, which is a schematic illustration of a screening system 40 for screening a GI tract 72 of a subject 54, in accordance with an embodiment of the present invention. System 40 is in many aspects generally similar to the screening system described in the '129 publication. System 40 typically comprises an ingestible capsule 50 and an external data-recording unit 52. For some applications, data-recording unit 52 is worn on a belt 59 around the subject's waist (as shown in FIG. 1) or elsewhere on the subject's body, such as the wrist (configuration not shown). Alternatively, for some applications, capsule 50 comprises an internal data-recording unit, and external data-recording unit 52 is not provided. In these applications, the data recorded by capsule 50 are retrieved after the capsule has been expelled from the body. In a typical screening procedure using system 40, an oral contrast agent 70 is administered to the subject. Contrast agent 70 is typically adapted to pass through the GI tract and be expelled with the feces, substantially without being absorbed into the blood stream. After the contrast agent is administered (e.g., several hours after the contrast agent is administered), subject 54 swallows capsule 50.

Figure 2:
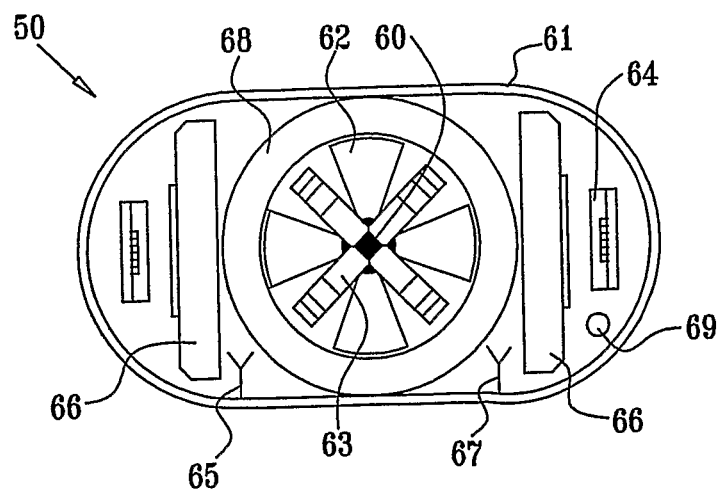
FIG. 2 is a schematic illustration of a capsule, in accordance with an embodiment of the present invention.

Reference is made to FIG. 2, which is a schematic illustration of capsule 50, in accordance with an embodiment of the present invention. Capsule 50 comprises at least one radiation source 60 adapted to emit gamma and/or x-rays (i.e., radiation having an energy of at least 10 keV), the source being disposed in a housing 61. Alternatively or additionally, radiation source 60, and/or an additional radiation source disposed within the capsule, emits beta radiation. Capsule 50 further comprises at least one gamma and/or or x-ray radiation detector 62, and, typically, at least one collimator 63 adapted to collimate the radiation produced by radiation source 60. Alternatively or additionally, detector 62, and/or an additional detector disposed within the capsule, is adapted to detect backscattered beta particles, and/or electrons generated in response to radiation emitted from source 60. For some applications, radiation source 60 comprises a radioisotope. Alternatively, radiation source 60 comprises a miniature radiation generator. Capsule 50 also typically comprises electronic circuitry 64, a power supply 66 (such as a battery), a wireless communication device for communicating with external data-recording unit 52, and a radiation shield 68. In some embodiments, the capsule comprises a pressure sensor 69. As appropriate for various applications, the wireless communication device may comprise electronic devices 65 and 67, which may comprise antennae or electrodes.

Typically, shield 68 is configured to shield the subject from emitted radiation when the capsule is not scanning the GI tract. In embodiments in which beta radiation is emitted from the capsule, the shield typically comprises a high-density ceramic material to stop electrons and at the same time to reduce secondary "stopping radiation" x-rays from being generated. In addition, a combination of a ceramic shield and a high atomic number metal shield on its outer perimeter may be used to reduce emission of secondary x-rays. Secondary x-rays are the result of Compton interaction of photons coming from source 60 through collimator hole 63 and hitting the capsule housing. Some of the photons from the Compton interaction on this surface return in the direction of detectors 62 and may be detected. In some embodiments, shield 68 reduces the number of photons reaching the detectors following this interaction.

In some embodiments of the present invention, radiation source 60, collimator 63, radiation shield 68, radiation detectors 62 and/or electronic circuitry 64 rotate during scanning. For example, the collimator and/or the detector may rotate through more than 270 degrees, e.g., through 360 degrees.

In some embodiments, as pressure sensor 69 senses changes of pressure related to contractions of the colon muscles, the capsule starts scanning by opening collimator 63 and exposing radiation source 60. Subsequently, radiation shield 68 and radiation detectors 62 start turning at a rate that is typically between 2 and 50 turns per second or, for some applications, between 50 and 500 turns per second. As each collimator 63 allows emission of gamma or x-ray photons to a specific angular sector, radiation detector 62 which turns together with the collimator detects the Compton backscattered photons, x-ray fluorescence photons, and/or electrons returning from the colon contents within that angular sector. In some embodiments, as the rotating portion of the capsule turns, it enables scanning of the whole circumference around the capsule, as the capsule moves forward due to the colon contents movement induced by the colon wall's contractions. In some embodiments, the radial scanning resolution of the capsule is varied by varying a rate of rotation of the rotatable portions of the capsule, and/or by varying the time interval over which the photon flux is integrated, per angular sector. For example, if, for each angular sector, the photon flux is integrated over a larger time period, then each angular sector will be greater, and there will be fewer angular sectors per rotation of the capsule.

For some applications, the capsule comprises a plurality of detectors. Each of the detectors rotates through less than 360 degrees, but the plurality of detectors scans 360 degrees. For example, the capsule may comprise two detectors, each of which can rotate through 180 degrees, such that in combination the two detectors are able to scan 360 degrees. Alternatively or additionally, the capsule comprises a plurality of collimators 63. Each of the collimators rotates through less than 360 degrees, but the plurality of collimators scans 360 degrees. For example, the capsule may comprises two collimators each of which can rotate through 180 degrees, such that in combination the two collimators are able to allow exposure of radiation source 60 to the 360 degrees circumference of the colon. For some applications, a part of the capsule rotates as described while the other part is generally stationary. For example, the stationary part may include a motor (not shown), a power supply (such as battery 66), pressure sensor 69 and/or a tilt sensor (not shown). For some applications, the transfer of signals and supply current from the stationary part of the capsule to the rotating part of the capsule is done via a slip ring, configured to transfer data signals and supply current. In some embodiments, a rotational encoder is incorporated into the capsule, to enable the electronic circuitry and the capsule software to track the rotational position of the rotating part of the capsule as it rotates. This allows the circuitry to associate each detected photon with its appropriate angular sector. For some applications, the rotational encoder is built into the slip ring by way of a non-continuous conducting surface on the slip ring divided into even sections (typically 4-128 sectors), that enable the electronic circuit to detect the position of the rotating slip ring as it turns. In some embodiments, the encoder comprises a marker, such as a missing sector position, in order to mark the completion of a 360 degree turn. For example, this may enable the electronics to resynchronize every turn, thus compensating for rotational speed variations or errors in the position detection.

For some applications, capsule 50 scans the colon at predefined time intervals to ensure scanning of the entire colon even when the capsule is moving very slowly and pressure changes are not sensed. For example, the capsule may scan the colon every 5-30 seconds, and/or every 0.5-5 minutes.

For some applications, radiation shield 68 is set to open collimators 63 only when the capsule senses movement of the capsule, for example, in response to pressure sensor 69 detecting pressure changes in the colon. In this manner, scanning of the colon and the exposure of the patient to radiation is generally limited to only those periods when the colon contents are moving, thus reducing the overall radiation exposure for the patient. In some embodiments, this saves power consumption, as scanning is done only when the capsule senses pressure changes.

In some embodiments, in response to capsule 50 detecting a pressure change indicative of a bowel movement, the capsule scans continuously as rapid movement through the colon is anticipated. Typically, in response to sensing a pressure change, the capsule scan continuously for a period of between 10 seconds and one minute, or between one minute and ten minutes. In some embodiments, movement of the capsule is detected using other sensing means.

In some embodiments, radio frequency (RF) transmission and reception is used to measure if capsule 50 is moving, and/or to detect a rate of movement of the capsule. For this, the capsule transmits a short RF pulse from electronic device 65 (e.g., an antenna) every few seconds, typically every 1-60 seconds, and receives the signal from electronic device 67 (e.g., another antenna), which is located at a different location on the capsule. If the capsule moved in the last time interval, then the received signal will have a different amplitude. Due to the low impedance and high attenuation of the colon contents, any changes in the relative position of the capsule in the colon alters the RF signal.

In some embodiments, low voltage pulse transmission and reception is used to measure if capsule 50 is moving and/or to detect a rate of movement of the capsule. For this, the capsule generates low frequency voltage pulses between two or more electronic devices 65 and 67 (e.g., electrodes) every few seconds, typically every 1-60 seconds, located at different locations on the capsule. If the capsule moved in the last time interval, the current induced by the voltage pulses will have a different amplitude due to the changes in impedance caused by changes in the relative position of the capsule in the colon.

In some embodiments, a magnetic flow meter, as is known in the art, is used to measure a rate of movement of capsule 50. Typically, a small magnet is placed close to or on the surface of capsule 50, and a magnetic field is applied across the colon. Two or more electrodes measure a voltage induced by movement of the magnet across the applied magnetic field. A rate of movement of the capsule is deduced from the strength of the induced voltage.

In some embodiments, capsule 50 and/or external data-recording unit 52 runs an adaptive algorithm to optimize the frequency of the scanning. The algorithm works by evaluating the differences in readings for all imaged sectors of the colon as a function of time. In an embodiment, the algorithm maintains a record of a given number of scan readings (e.g., the count rate of Compton backscattered photons for each of the given number of scan readings) for each sector, and calculates the average for these past sectors. Then, the algorithm compares the current reading with this average. If the difference between the square of the average and the current reading is below a lower threshold, the next reading is set to be taken following a longer time interval than the previous time interval. Typically, there is a maximum time interval beyond which the time interval is not extended. If the difference between the square of the average and the current reading is greater than an upper threshold, the next reading is taken following a shorter time interval than the previous time interval. If the difference between the square of the average and the current reading is between the upper and lower thresholds, then the time interval until the next reading is taken is kept constant.

In some embodiments, the adaptive algorithm evaluates the differences in pressure readings as a function of time. For example, the algorithm may maintain a record of a few past pressure readings, and calculate the average and standard deviation for these past time pressure measurements. Then, the algorithm compares the current pressure reading with this average, and if the difference of the square of the average and the new reading is larger than a certain threshold, the capsule starts scanning, or scans at a higher rate than it was scanning previously. In some embodiments, the threshold is adaptively set based on the average of the past few readings and the standard deviation of these readings. Typically, the capsule begins scanning in response to detecting a pressure that is one to ten standard deviations, or a given value plus one to ten standard deviations, greater than the average of the given number of previous readings.

In some embodiments, respective images are generated in response to data detected by radiation detector 62. The adaptive algorithm is used to detect movement, and/or a rate of movement of the capsule by comparing respective images to each other. In some embodiments, the adaptive algorithm is applied in response to the capsule detecting a change in pressure. Typically, the algorithm varies the time interval between successive scans of the capsule in response to detecting movement and/or a rate of movement of the capsule. In some embodiments, the algorithm constructs an image that is the average of the previous several images, then the algorithm compares the current image to the average image. Typically, the algorithm varies the time interval between successive scans of the capsule in response to detecting movement and/or a rate of movement of the capsule. In some embodiments, the algorithm is initiated in response to the pressure sensor detecting a change in pressure.

In an embodiment of the present invention, a tilt sensor is employed in a stationary part of the capsule to monitor the 3D tilt angle of the capsule, relative to the earth's center of gravity. This information is used by the capsule to sense turning while scanning in order to readjust the frame of reference during post processing. This information is typically transmitted from the capsule to external data-recording unit 52.

In some embodiments, data regarding the tilt angle of the capsule, pressure changes of the capsule, and/or acceleration of the capsule are used to identify when the capsule is expelled from the subject's anus. Typically, in response to detecting the expulsion of the capsule, data from the capsule are immediately transmitted to external data-recording unit 52.

In some embodiments, radiation source 60 emits beta radiation, and the emitted high-energy electrons interact directly with the colon contents, tissue of the colon wall, and tissue outside the colon. The electrons are scattered by these interactions, and a portion of the electrons backscatter at various energy levels, and are detected by detector 62. The emitted electrons typically have an energy of greater than 1 mega-electron volt (MeV), e.g., between 1.5 and 7 MeV. For example, the emission of primarily beta radiation, rather than of gamma and/or x-ray radiation, may allow the use of less radiation, because electrons interact with matter with higher probability than do photons. Furthermore, beta radiation has a maximum range which depends on the energy of the electrons. For example, the electrons emitted by Y-90 have a maximum range of 11 mm in water. Therefore, exposure to radiation is limited, such that tissue outside the colon has limited or no radiation exposure.

For some applications, electron backscattering is used to sense small changes in tissue densities near capsule 50. This, in turn, is used to differentiate between a) tubular and villous polyps and b) neoplastic polyps. Tubular and villous polyps typically have a higher density than do neoplastic polyps. Tubular and villous polyps are more likely than neoplastic polyps to become cancerous. In some embodiments, the emitted beta radiation generates electrons and/or XRF photons in the colon.

In some embodiments of the invention, electrons and/or photons generated in response to beta radiation are detected and used to quantify the density of the tissue that is close to the capsule. This information can be useful for physicians to classify polyps as either a) tubular or villous, or b) neoplastic.

In some embodiments, radiation source 60 emits beta radiation and also gamma and/or x-ray radiation. For example, the beta radiation may be used for detection at close ranges from the capsule with high sensitivity, whereas the gamma and/or x-ray radiation may be more sensitive for longer ranges from the capsule. In such embodiments, detector 62 typically detects backscattered electrons as well as backscattered Compton photons and XRF photons. In some embodiments, the capsule contains a first radiation source that emits photons, and an additional source that emits beta radiation. In some embodiments, the capsule contains a first radiation detector that detects photons, and an additional detector that detects beta radiation.

In some embodiments of the present invention, Compton backscatter generated in response to emitted x-ray and/or gamma photons is used to quantify the density of the tissue that is close to the capsule. This information can be useful for physicians to classify polyps as either a) tubular or villous, or b) neoplastic.

In some embodiment of the present invention, Compton backscatter and XRF photons generated in response to emitted x-ray and/or gamma photons, are used to quantify the density of the tissue that is close to the capsule. Typically, this is accomplished by correlating the variations in XRF photon flux with variations in Compton backscattering photon flux, as described in the paragraph below. Variations in Compton backscattering photon flux which are not correlated with corresponding variations in x-ray fluorescence photon flux are interpreted to indicate changes in tissue density. This may be used to classify polyps as a) tubular or villous, or b) neoplastic.

In response to the radiation emitted by source 60, XRF photons are typically only emitted from the colon contents, which contain contrast agent 70. Compton backscattered photons are emitted from the colon contents as well as from the tissue of the colon walls and beyond. Therefore, in some embodiments, the XRF photon flux is normalized and then subtracted from the Compton photon flux, to enable an automatic evaluation of the photon flux that is related to tissue of the colon and beyond. Typically, the difference between the normalized XRF photon flux and the Compton photon flux is mainly due to the tissue of the colon, since Compton photon flux is proportional to the square root of the distance from the capsule to the tissue surface. Compton photon flux is further dependent on the density of the tissue. Therefore, by analyzing the Compton photon flux, an automated algorithm provided by some embodiments of the present invention determines the density of the tissue from which the Compton photons were backscattered.

Figure 3A:
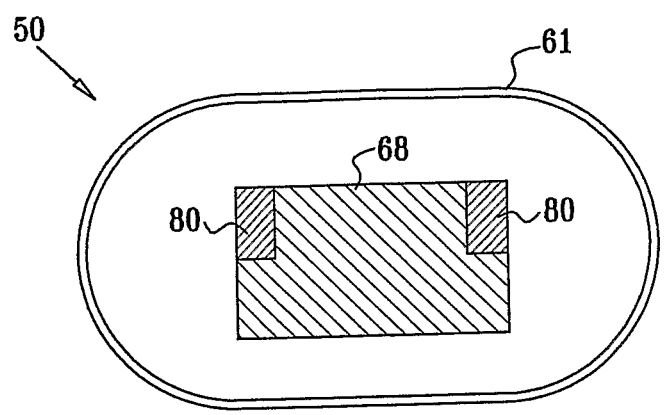
FIGS. 3A-B are schematic illustrations of a capsule that comprises shield wings, in accordance with an embodiment of the present invention.
Figure 3B:
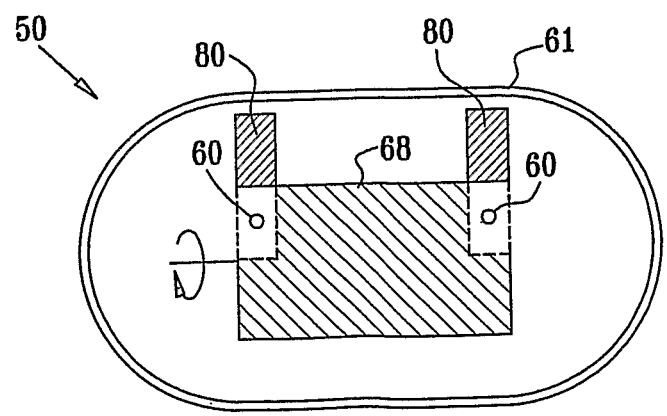

Reference is now made to FIGS. 3A-B, which are schematic illustrations of radiation shield 68 of capsule 50 comprising shield wings 80, in accordance with an embodiment of the present invention. In an embodiment of this invention, when the capsule is not scanning the GI tract, the shield wings are closed (as shown in FIG. 3A), and the subject is shielded from radiation source 60. To initiate scanning of the GI tract, radiation source 60 is exposed by rotating shield 68 together with the detectors 62, so that centrifugal force acts on shield wings 80 causing them to open and expose source 60 (as shown in FIG. 3B). When not rotating, shield wings 80 are typically held closed using a spring. The rotating shield wings are disposed within housing 61 of capsule 50, to avoid contact between moving parts of the capsule and the wall of the colon. In other embodiments, other techniques are employed to move shield 68 and/or source 60 (e.g., by activation of a solenoid).

Figure 4A:
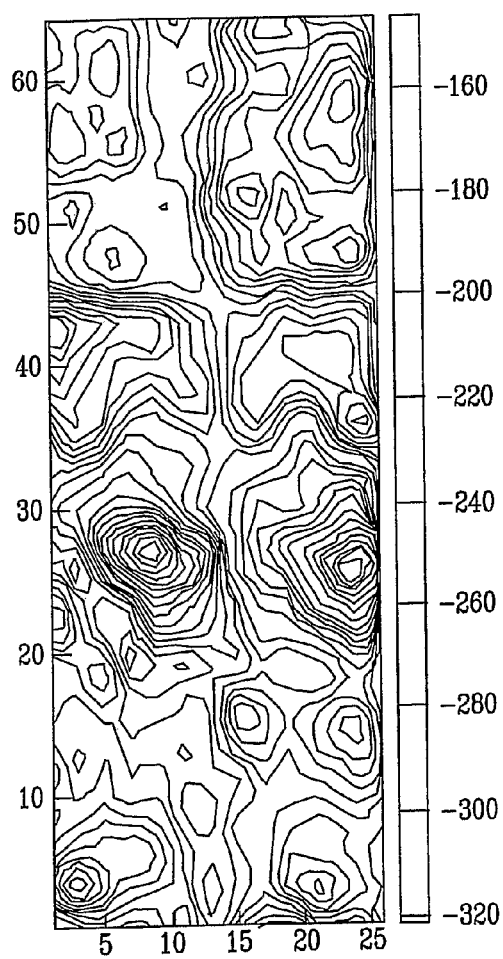
FIGS. 4A-B are height maps respectively of a flat polyp and of a polyp with a stalk, both of which polyps were induced in a pig's colon, the maps having been generated in accordance with an embodiment of the present invention.
Figure 4B:
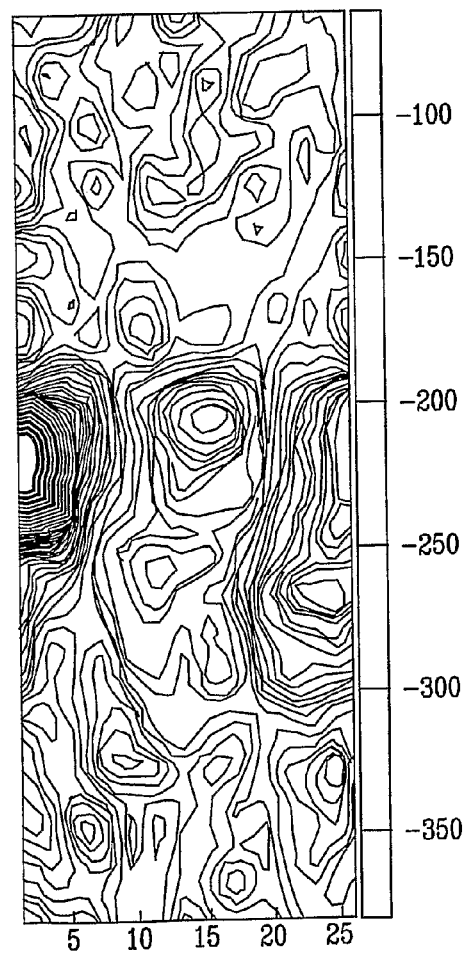

Reference is now made to FIGS. 4A-B, which are height maps of respective polyps which were induced in the colons of respective first and second pigs, the height maps having been generated in accordance with an embodiment of the present invention. In some embodiments of the invention, a processing algorithm is employed to distinguish between polyps with stalks and polyps without stalks. The algorithm typically relies on the fact that the capsule is very likely to contact any polyps larger than a few millimeters (e.g., larger than 6 mm), since the colon walls contract in order to push the capsule forward. This contact with the polyp causes the polyp to align along the path of the capsule, hence stretching the polyp along the longitudinal axis of the colon as the capsule travels near the polyp. This stretching of the polyp reveals the stalk of the polyp to the capsule as it passes the polyp. The stretching of the polyp typically generates asymmetry in the image of the polyp, as the center of the polyp is dragged in the direction of the capsule's movement.

FIG. 4A is a height map of a flat polyp that was induced in the colon of a first pig, the map having been generated using apparatus described hereinabove. FIG. 4B is a height map of a polyp with a stalk induced in the colon of a second pig. A difference can be observed in the shape of the respective height maps, the map of FIG. 4B having an elongated tail associated with the polyp with the stalk. The direction of motion of the capsule was upward on the page, and, the polyp was dragged in that direction. In some embodiments, the likelihood that a polyp is potentially cancerous is assessed by determining if the polyp has a stalk. (Clinical studies of polyps and their progress to cancer suggest that those with stalks are less likely to become cancerous, whereas polyps without stalks—flat polyps—are more likely to become cancerous.)

In some embodiments of the invention, a distance between the capsule and the wall of the colon at any given point is estimated. In addition, the size of a polyp or any other structure within the colon is estimated. To enable these estimations, the flux of XRF and the flux of Compton backscattered photons are measured simultaneously in a large number of measurements throughout the colon, and these values are recorded for post-processing. The concentration of contrast agent typically varies along the colon. Furthermore, XRF photon flux and Compton photon flux both vary in relation to the contrast agent concentration. Therefore, by detecting XRF and Compton backscattering data along the colon, it is possible to estimate the actual distance between the capsule and the wall of the colon, and the actual size of features in the colon. This is done by simultaneously solving equations relating XRF and Compton photon flux to two unknowns, distance and the contrast agent concentration.

For x-ray fluorescence (XRF), the equation that describes the distance between the capsule and the wall of the colon, as a function of photon flux detected, is:

$$Lxrf = Kxrf*[Ln(Ixrf)/(-\mu xrf*\rho)]$$

where Lxrf is the estimated distance between the capsule and the colon wall, Kxrf is a known scalar constant, ad is the XRF photon flux which is measured, µxrf is the known XRF interaction probability, and ρ is the contrast agent concentration.

For Compton backscattering (COMP), the equation that describes the distance between the capsule and the colon wall, as a function of photon flux detected, is:

$$Lcomp = Kcomp*(Ln(1-Icomp)/-\mu comp*\rho)$$

where Lcomp is the estimated distance between the capsule and the colon wall, Kcomp is a known scalar constant, Icomp is the Compton photon flux which is measured, µcomp is the known Compton interaction probability, and ρ is the contrast agent concentration.

Since at any point along the colon, these two estimations represent the same true distance, the two equations can be solved simultaneously as there are only two unknowns, namely the true distance L between the capsule and the colon wall and the contrast agent concentration (ρ). The simultaneous equations to be solved are:

$$L = Kxrf*[(Ln(Ixrf)/(-\mu xrf*\rho)] \quad \text{(Equation 1)}$$

$$L = Kcomp*[Ln(1-Icomp)/(-\mu comp*\rho)] \quad \text{(Equation 2)}$$

The colon is divided into sections called haustra. Typically, within each haustrum, the contrast agent concentration remains approximately constant. The concentration of the contrast agent typically changes between adjacent haustra. Typically, the length of each haustrum is 20 mm to 40 mm. In some embodiments, multiple measurements are taken within each haustrum to provide the average contrast agent concentration for that haustrum. Typically, the simultaneous equations provided hereinabove, are solved, for each haustrum, using the average XRF and Compton photon flux readings taken from a plurality of positions (e.g., 2 to 20, or 20 to 40 readings) within the haustrum (e.g., positions within a section of the colon that is 20 mm to 40 mm in length). Within each haustrum, the contrast agent can be assumed not to have changed substantially, and the simultaneous equations using the average photon fluxes are solved to provide the average contrast agent concentration for that haustrum. Typically, equations 1 and 2 are then solved to provide the distance of the capsule from the colon wall, for each of the individual readings within the haustrum, using, for the contrast agent concentration, the average contrast agent concentration of the haustrum.

In some embodiments, a moving average of, for example, 2 to 20, or of 20 to 40, readings of the XRF and Compton photon flux is calculated, for every 20 mm to 40 mm of the length of the colon. For each average Compton and XRF photon flux, a standard deviation of the average is calculated. Typically, the standard deviation of the average photon flux changes when the capsule moves from one haustrum to the next. In some embodiments, an algorithm determines a set of averaged readings that corresponds to readings taken within the same haustrum by detecting a change in the standard deviation of the moving averaged readings. The average contrast agent concentration within that haustrum is then determined by solving, for that haustrum, the simultaneous equations disclosed hereinabove.

The scope of the present invention includes embodiments described in the following applications, which are incorporated herein by reference. In an embodiment, techniques and apparatus described in one or more of the following applications are combined with techniques and apparatus described herein:

International Patent Application PCT/IL2004/001140, filed Dec. 16, 2004, entitled, "Intra-lumen polyp detection," or U.S. patent application Ser. No. 10/596,065, filed in the national phase thereof;

U.S. Provisional Patent Application 60/531,690, filed Dec. 17, 2003, entitled, "Intra lumen polyp detection"; and/or U.S. Provisional Patent Application 60/559,695, filed Mar. 31, 2004, entitled, "Intra-lumen polyp detection."

It will be appreciated by persons skilled in the art that the present invention is not limited to what has been particularly shown and described hereinabove. Rather, the scope of the present invention includes both combinations and sub combinations of the various features described hereinabove, as well as variations and modifications thereof that are not in the prior art, which would occur to persons skilled in the art upon reading the foregoing description.

The invention claimed is:

1. An apparatus, comprising: a capsule configured to be swallowed by a subject and to pass through a gastrointestinal (GI) tract of the subject, the capsule comprising:
    a capsule housing;
    at least one radiation source configured to emit radiation from the capsule;
    a rotatable collimator configured to rotate with respect to the housing and to collimate the radiation emitted by the at least one radiation source;
    at least one radiation detector positioned next to the collimator and coupled with the collimator to rotate together, the radiation detector being configured to detect radiation comprising particles generated responsive to the radiation emitted from the capsule, wherein the generated particles that are detected are directed back toward the radiation detector and collimator in an opposite direction of the radiation emitted from the capsule;
    electronic circuitry programed to serve as a control unit to analyze data regarding the detected particles; and
    a shield for covering and uncovering the radiation source, the shield is configured to rotate with the collimator and detector and comprises wings that cover openings on the shield, the wings are configured to rotate open and expose the radiation source;
    wherein the wings are disposed on the shield, within the capsule housing to avoid contact with walls of the gastrointestinal tract; and wherein the wings are held closed by a spring when the shield is not rotating.

2. The apparatus according to claim 1, wherein the at least one radiation source is configured to emit one or more particles selected from a group consisting of: photons, gamma radiation, beta radiation and electrons.

3. The apparatus according to claim 1, wherein the at least one radiation detector is configured to detect one or more particles selected from a group consisting of:
    photons, Compton backscattering photons, x-ray fluorescence (XRF) photons, and electrons.

4. The apparatus according to claim 1, wherein the control unit analyzes data regarding the detected particles in order to generate information useful for identifying a clinically-relevant feature of the GI tract of the subject.

5. The apparatus according to claim 1, wherein the control unit is configured to detect that the capsule has reached a predetermined area within the GI tract, and to initiate rotation of the collimator in response to detecting that the capsule has reached the predetermined area.

6. The apparatus according to claim 1, wherein the predetermined area is an area of clinical interest.

7. The apparatus according to claim 1, wherein the at least one radiation detector is configured to rotate with respect to the housing and to detect particles generated responsively to the emitted radiation.

8. The apparatus according to claim 1, wherein the control unit is configured to determine tissue density from the analyzed data.

9. The apparatus according to claim 8, wherein the control unit is configured to distinguish between polyps based on the determined tissue density.

10. The apparatus according to claim 1, wherein the control unit is part of the capsule.

11. The apparatus according to claim 1, wherein the at least one radiation detector detects in response to the emitted radiation a first signal and a second signal inside the GI tract of the subject, and wherein the control unit processes the first signal to generate a first image of the GI tract of a region where the first signal was detected, and wherein the control unit processes the second signal to generate a second image of the GI tract of a region where the second signal was detected; and detects movement of the capsule relative to the GI tract by comparing the first and second generated images.

12. A method comprising:
    orally administering a capsule in a housing to a subject to analyze a gastrointestinal (GI) tract, said capsule comprising a radiation source collimated by a collimator and at least one radiation detector positioned next to the collimator and coupled thereto to rotate together directing the radiation around an inner circumference of a portion of the GI tract;
    covering the radiation source, collimator and detector with a shield, the shield having openings covered by wings that can be rotated open to expose the radiation source;
    rotating the shield, collimator and detector, causing the wings to rotate open and uncover the openings of the shield exposing the radiation source; wherein the wings are disposed on the shield, within the capsule housing to avoid contact with walls of the gastrointestinal tract; and wherein the wings are held closed by a spring when the shield is not rotating;
    detecting with the at least one radiation detector radiation generated in response to the radiation emitted from the capsule, wherein generated particles that are detected are directed back toward the radiation detector and collimator in an opposite direction of the radiation emitted from the capsule; and
    generating information useful for identifying a clinically-relevant feature of the GI tract of the subject by analyzing data regarding the detected radiation.

13. The method according to claim 12, wherein the emitted radiation comprises particles selected from a group consisting of: photons, gamma radiation, beta radiation and electrons.

14. The method according to claim 12, wherein the detected radiation comprises particles selected from a group consisting of: photons, beta radiation, Compton backscattering photons, x-ray fluorescence (XRF) photons, and electrons.

15. The method according to claim 12, wherein the useful information provides an indication of tissue density.

16. The method according to claim 15, and further quantifying the indicated tissue density to distinguish between polyps.

17. The method according to claim 12, further comprising detecting when the collimator has reached a predetermined area, and initiating rotation of the collimator in response to detecting that the collimator has reached the predetermined area.

18. The method of claim 12, wherein said detecting step includes detecting in response to the emitted radiation a first signal and a second signal inside the subject's GI tract, the method further comprising:

processing the first signal to generate a first image of the GI tract in a region where the first signal was detected;

processing the second signal to generate a second image of the GI tract in a region where the second signal was detected; and determining movement of the capsule in the GI tract by comparing the first and second images.

19. The method according to claim 12, wherein the step of rotating the shield includes moving a first portion of the radiation shield relative to a second portion of the radiation shield to uncover the radiation source due to centrifugal force induced by rotation of the shield.

20. The apparatus according to claim 1, wherein the radiation shield includes a first portion and a second portion, the second portion configured to move relative to the first portion to uncover the radiation source due to centrifugal force induced by rotation of the shield.

* * * * *